United States Patent
Bardina et al.

(10) Patent No.: US 9,753,015 B2
(45) Date of Patent: Sep. 5, 2017

(54) CHARACTERIZATION AND/OR DETECTION OF STRUCTURAL CHARACTERISTICS ASSOCIATED WITH SYRINGES AND/OR AUTOMATIC INJECTION DEVICES BASED ON ACOUSTICS

(71) Applicant: AbbVie Biotechnology Ltd., Hamilton (BM)

(72) Inventors: Jose L. Bardina, Buffalo Grove, IL (US); Jovo Dragicevic, Gurnee, IL (US); Jose M. Rodriguez, Gurnee, IL (US); Lewis H. Sita, Kildeer, IL (US)

(73) Assignee: AbbVie Inc., North Chicago, IL (US)

( * ) Notice: Subject to any disclaimer, the term of this patent is extended or adjusted under 35 U.S.C. 154(b) by 91 days.

(21) Appl. No.: 14/434,050

(22) PCT Filed: Oct. 11, 2013

(86) PCT No.: PCT/US2013/064483
§ 371 (c)(1),
(2) Date: Apr. 7, 2015

(87) PCT Pub. No.: WO2014/059240
PCT Pub. Date: Apr. 17, 2014

(65) Prior Publication Data
US 2015/0253289 A1 Sep. 10, 2015

Related U.S. Application Data

(60) Provisional application No. 61/713,234, filed on Oct. 12, 2012.

(51) Int. Cl.
*G01N 29/04* (2006.01)
*G01N 29/12* (2006.01)
(Continued)

(52) U.S. Cl.
CPC ............ *G01N 29/12* (2013.01); *A61M 5/178* (2013.01); *A61M 5/5086* (2013.01); *G01H 1/00* (2013.01);
(Continued)

(58) Field of Classification Search
CPC ..... G01N 29/12; G01N 29/045; A61M 5/178; A61M 5/5086; G01M 7/022; G01M 7/025; G01M 7/027
See application file for complete search history.

(56) References Cited

U.S. PATENT DOCUMENTS

| 3,307,696 A | 3/1967 | Sager |
| 3,556,079 A * | 1/1971 | Omizo ..................... A61B 8/06 600/461 |

(Continued)

FOREIGN PATENT DOCUMENTS

| EP | 2135068 A1 | 12/2009 |
| EP | 2381246 A1 | 10/2011 |

(Continued)

OTHER PUBLICATIONS

Belyaev, A., et al. "Crack detection and analyses using resonance ultrasonic vibrations in full-size crystalline silicon wafers." Applied physics letters, 88(11), (Mar. 15, 2006): 111907.

(Continued)

*Primary Examiner* — Helen Kwok
(74) *Attorney, Agent, or Firm* — McCarter & English, LLP; David R. Burns

(57) ABSTRACT

System and methods for characterizing and/or detecting structural characteristics of syringes (e.g., bare syringes or syringes included in automatic injection devices) using acoustic vibrations. A transducer is positioned proximate to a syringe so that the transducer vibrates at one or more frequencies and a response of the syringe to the vibrations (Continued)

can be received via the receiver. The response of syringe can be processed to determine a structural characteristic of the syringe.

25 Claims, 13 Drawing Sheets

(51) Int. Cl.
*A61M 5/50* (2006.01)
*G01H 1/00* (2006.01)
*G01M 7/02* (2006.01)
*A61M 5/178* (2006.01)
*G01H 17/00* (2006.01)
*A61M 5/20* (2006.01)

(52) U.S. Cl.
CPC ............ *G01M 7/022* (2013.01); *G01M 7/025* (2013.01); *G01M 7/027* (2013.01); *G01N 29/045* (2013.01); *A61M 5/20* (2013.01); *A61M 2209/02* (2013.01); *G01H 17/00* (2013.01); *G01N 2291/0289* (2013.01); *G01N 2291/2698* (2013.01)

(56) References Cited

U.S. PATENT DOCUMENTS

| | | | |
|---|---|---|---|
| 5,408,880 A | 4/1995 | Rhodes et al. | |
| 5,615,007 A * | 3/1997 | Matsuura | G01N 21/90 356/237.1 |
| 5,821,424 A | 10/1998 | Rodriguez | |
| 6,171,276 B1 * | 1/2001 | Lippe | A61M 5/20 128/DIG. 1 |
| 6,413,789 B2 | 7/2002 | Ostapenko | |
| 7,007,443 B2 * | 3/2006 | Liedtke | B65B 15/04 53/399 |
| 8,147,479 B1 * | 4/2012 | Wach | A61M 5/16831 604/522 |
| 8,161,810 B2 * | 4/2012 | Cadieux | A61M 5/14546 73/1.73 |
| 2003/0089727 A1 * | 5/2003 | Osborne | B65B 3/003 221/70 |
| 2005/0087016 A1 | 4/2005 | Gilmore et al. | |
| 2006/0259195 A1 * | 11/2006 | Eliuk | A61J 1/20 700/245 |
| 2009/0187136 A1 * | 7/2009 | Babaev | A61M 5/31511 604/22 |
| 2009/0249879 A1 | 10/2009 | Jeyaraman et al. | |
| 2010/0138027 A1 | 6/2010 | Ostapenko | |
| 2013/0184676 A1 * | 7/2013 | Kamen | G06F 19/3406 604/506 |
| 2014/0250517 A1 * | 9/2014 | Kim | H04L 9/3228 726/7 |

FOREIGN PATENT DOCUMENTS

| | | |
|---|---|---|
| FR | 2846096 A1 | 4/2004 |
| JP | 2005283204 A | 10/2005 |
| WO | 2008112597 A1 | 9/2008 |

OTHER PUBLICATIONS

Dallas, W., O. Polupan, and S. Ostapenko. "Resonance ultrasonic vibrations for crack detection in photovoltaic silicon wafers." Measurement Science and Technology 18, No. 3 (Feb. 5, 2007): 852.
International Search Report and Written Opinion by the International Searching Authority for International Application No. PCT/US2013/064483 dated Jan. 16, 2014.

* cited by examiner

CHARACTERIZATION AND/OR DETECTION OF STRUCTURAL CHARACTERISTICS ASSOCIATED WITH SYRINGES AND/OR AUTOMATIC INJECTION DEVICES BASED ON ACOUSTICS

RELATED APPLICATIONS

This application is a 35 U.S.C. §371 national stage filing of International Application No. PCT/US2013/064483, filed on Oct. 11, 2013, which claims priority to U.S. Provisional Patent Application Ser. No. 61/713,234 filed on Oct. 12, 2012. Each of the foregoing applications is incorporated by reference herein in its entirety.

BACKGROUND

Exemplary embodiments of the present disclosure relate to characterizing and/or detecting structural characteristics of syringes, and more particularly to characterizing and/or detecting structural characteristics of syringes and/or automatic injection devices using acoustic vibrations.

One of the most common routes of administration for medications is by injection, such as intravenous, subcutaneous or intramuscular injection. Typically, injections via a syringe are carried out by trained medical personnel and/or by a patient trained in the use of the syringe to allow for self-injection. Syringes can be used in a standalone form and/or can be incorporated into automatic injection devices (autoinjectors). Standalone syringes are generally bare, i.e., unencumbered by a housing, while syringes incorporated in automatic injection devices are generally at least partially surrounded by and/or encased in a housing.

Automatic injection devices have been used, for example, to deliver medications under emergency conditions, such as to administer epinephrine to counteract the effects of a severe allergic reaction, for example, as caused by a food allergy. Automatic injection devices also have been described for use in administering antiarrhythmic medications and selective thrombolytic agents during a heart attack.

In some instances syringes can have structural abnormalities that may include structural defects and/or damage that occurred during manufacture, warehousing, and/or shipping of the syringes and/or automatic injection devices including the syringes. For example, the syringes may include cracks and/or scratches as well as other structure abnormalities. Inspection of syringes for structural abnormalities is conventionally performed using visual or optical inspection processes. However, these processes are typically insufficient for detecting small cracks or closed cracks in syringes. Furthermore, these processes are generally not available when a large portion of the syringe is not visible and/or inaccessible, for example, because the syringe is encased in an automatic injection device. Conventionally, an automatic injection device is destroyed or disassembled to inspect a syringe incorporated in the automatic injection device.

SUMMARY

Exemplary embodiments include systems, methods, and non-transitory computer-readable mediums to facilitate the non-destructive characterization and testing of bare syringes and/or syringes included in automatic injection devices for structural abnormalities including for example, cracks and scratches. Exemplary embodiments can be implemented on standalone syringes as well as for syringes incorporated in automatic injection devices for which access to and/or visibility of the syringe is limited. Exemplary embodiments can use acoustic vibrations to induce a response in the syringe, which can be measured and used to characterize and/or test the syringe to provide an automated, non-destructive, efficient, and effective approach to identifying structural characteristics of syringes.

In one embodiment, a system including a transducer, a receiver, and a processing device is disclosed. The transducer outputs a first signal proximate to a syringe. The receiver receives a response of the syringe to the first signal. The processing device controls the transducer and the receiver to determine a structural characteristic of the syringe based on the response received the receiver.

In yet another embodiment, a system for characterizing a syringe based on structural characteristics of the syringe is disclosed. The system includes a transducer, a receiver, and a syringe characterization unit. The transducer is configured to vibrate at one or more frequencies. The receiver detects a syringe response to vibrations of the transducer. The syringe characterization unit is configured to characterize the response detected by the receiver.

In still another embodiment, a non-transitory computer readable medium that stores executable instructions executable by a processing device is disclosed. Execution of the instructions by the processing device causes the processing device to control a transducer to vibrate at one or more frequencies, receive a response of a syringe to vibrations of the transducer, and process the response to determine a structural characteristic of the syringe based on the response received the receiver.

In yet another embodiment, a method of detecting unacceptable structural abnormalities of syringe is disclosed. The method includes inducing vibrations in one or more syringes and measuring a response of the syringe to the vibrations.

BRIEF DESCRIPTION OF THE DRAWINGS

The foregoing and other objects, features and advantages of exemplary embodiment of the present disclosure will be more fully understood from the following description of exemplary embodiments when read together with the accompanying drawings, in which:

FIG. 16 illustrates a perspective view of an exemplary automatic injection device in which caps that cover proximal and distal ends of the housing are removed.

DETAILED DESCRIPTION OF EXEMPLARY EMBODIMENTS

Figure 1:
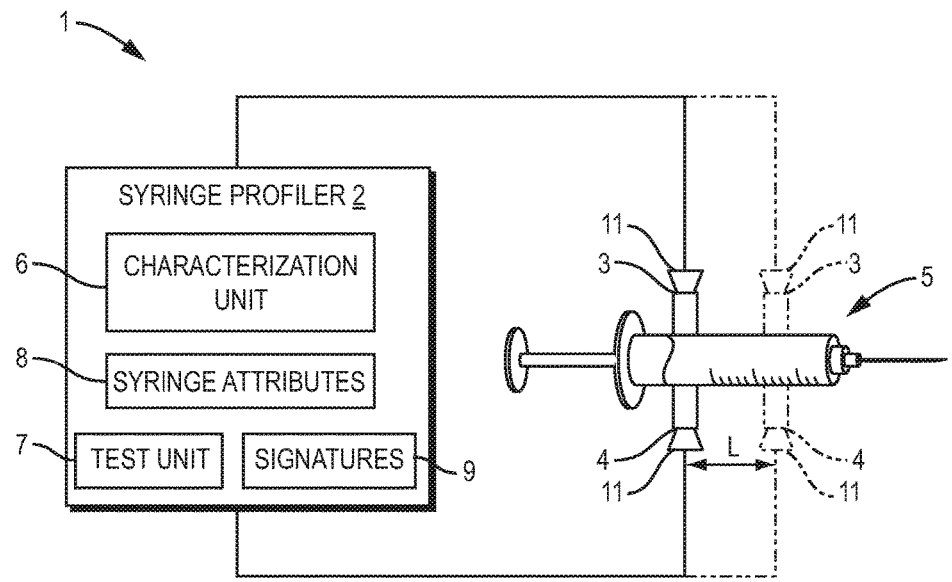
FIG. 1 illustrates an exemplary embodiment of a syringe characterization and testing system configured to determine a characteristic associated with a bare syringe.

Exemplary embodiments are provided for characterizing and/or detecting structural abnormalities of syringes (e.g., bare syringes and/or syringes included in autoinjectors) using acoustic vibrations. In exemplary embodiments, a transducer can be configured to emit one or more output signals at one or more frequencies to induce a response by a syringe, and a receiver can be configured to detect and/or measure parameters associated with the response. For example, the transducer can be configured to emit ultrasonic vibrations at or near a resonance frequency associated with a given syringe. Parameters associated with the response of the syringe to the output signal of the transducer can be used to characterize the syringe and/or to detect/identify structural characteristics of the syringe, such as cracks and/or scratches. For example, structural characteristics can be characterized and/or detected based on a peak amplitude of the response, a bandwidth of the response, and/or a frequency at which the peak amplitude of the response occurs.

Exemplary embodiments can operate based on an assumption that like syringes having like conditions respond similarly to a given stimuli and that like syringes having different conditions respond differently to a given stimuli. That is, a response to a given stimuli by a syringe having no structural abnormalities or acceptable structural abnormalities (e.g., a "good" syringe) can differ from a like syringe having structural abnormalities or unacceptable structural abnormalities (e.g., a "damaged" syringe). For example, response parameters, such as a peak amplitude, a response bandwidth, and/or a frequency at which the peak amplitude occurs can measurably and/or statistically differ between two like syringes for which one syringe has no structural abnormalities and the other syringe has structural abnormalities.

Before continuing with the detailed description, certain terms are defined, as follows:

As used herein, a "standalone syringe" is intended to refer to an unencumbered syringe that typically has a plunger which is manually actuated by the administrated of the injection by, for example, depressing a plunger to expel the contents of the syringe (e.g., a therapeutic agent).

As used herein, an "automatic injection device" (or "autoinjector") is intended to refer to a device that enables an individual (also referred to herein as a user or a patient) to self-administer a dosage of a therapeutic agent, such as a liquid medication, wherein the device differs from a standard syringe by the inclusion of a mechanism for automatically delivering the therapeutic agent to the individual by injection when the mechanism is engaged.

As used herein, the term "pre-filled syringe" is intended to encompass a syringe that is filled with a therapeutic agent prior to purchase from a pharmacy or other seller of medical devices and/or therapeutic agents.

As used herein, the term "signature" refers to one or more identifying characteristics of like syringes having like conditions. For example, a signature can include upper and/or lower limits for acoustic vibration response parameters based on a characterization of like syringes having like conditions such that syringes with acoustic vibration response within the upper and lower limits can be defined as having the same signature.

Characterization and Detection of Structural Abnormalities of Syringes

FIG. 1 illustrates an exemplary syringe characterization and defect detection system 1. The system 1 includes a syringe profiler 2 operatively coupled to at least one transducer 3 and at least one receiver 4. The system 1 can be configured and/or programmed to expose a syringe 5 to acoustic vibrations radiating from the transducer 3 and in turn, to measure a response of the syringe 5 to the acoustic vibrations emitted by the transducer 3. The response of the syringe 5 to the acoustic vibrations can vary based on attributes of the syringe 5. Some syringe attributes can include, but are not limited to a syringe length, diameter, surface area, body thickness, syringe contents (e.g., empty, pre-filled, composition of fill, volume of fill), syringe surroundings (e.g., a syringe housed in an automatic injection device or a standalone syringe), as well as other syringe attributes. For example, a pre-filled syringe and an empty syringe can have a different response to substantially similar acoustic vibrations. Likewise, a syringe housed in an automatic injection device and a standalone syringe can have a different response to a substantially similar acoustic vibration.

Figure 3:
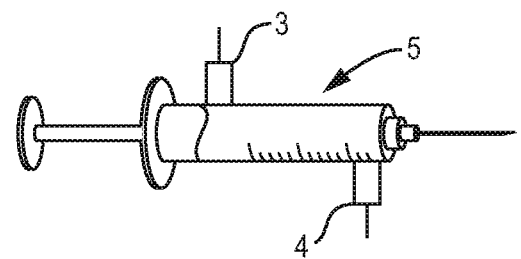
FIG. 3 illustrates an exemplary position of transducers and receivers with respect to a syringe body in accordance with an exemplary embodiment of the present disclosure.
Figure 4:
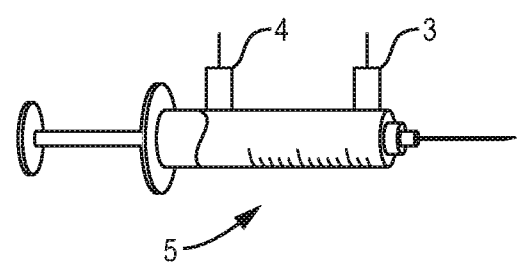
FIG. 4 illustrates another exemplary position of transducers and receivers with respect to a syringe body in accordance with an exemplary embodiment of the present disclosure.

The syringe profiler 2 can include a characterization unit 6 programmed and/or configured to implement a characterization process stored in memory and/or other non-transitory computer-readable memory (e.g., FIG. 3) and a test unit 7 programmed and/or configured to implement a test process stored in memory and/or other non-transitory computer-readable memory (e.g., FIG. 4). The profiler 2 can also include syringe attributes 8 associated with syringes, and syringe signatures 9 that are based on response parameters and syringe attributes. The profiler 2 can control and/or instruct the transducer 3 to generate acoustic vibrations. In exemplary embodiments, the profiler 2 can transmit signals to the transducer 3 that are based on the attributes 8 of the syringe 5, whether the syringe 5 is being characterized, and/or based on whether the syringe 5 is being tested to identify structural characteristics of the syringe 5 based on previously characterized syringes. The profiler 2 can programmed and/or configured to receive signals corresponding to the response of the syringe 5 via the receiver 4 and process those signals using the characterization unit 6 and/or the test unit 7. In exemplary embodiments, the profiler 2 and/or components thereof can be implemented using hardware, software, and/or a combination of hardware and software designed and/or programmed to perform the operational functions associated with the profiler 2, e.g., the characterization process, test process, and/or any other operations or processes to be implement by the profiler 2 in accordance with the present disclosure.

The characterization unit 6 is programmable and/or configurable to characterize syringes to generate the syringe signatures 9 to be used by the test unit 7 when detecting structural characteristics of a syringe. The characterization unit 6 can be programmed and/or configured to instruct or drive the transducer to vibrate at one or more frequencies and to receive a response of a syringe to the vibrations using the receiver 4. The characterization unit 6 can be programmed and/or configured to identify response parameters including, for example, a peak amplitude of the response, a frequency at which the peak amplitude occurs, and/or a bandwidth of the response. Using the response parameters of one or more syringes, the characterization unit 6 can be programmed and/or configured to generate a signature, which can include parameter limits to be used to detect a structural characteristic associated with a syringe (e.g., a crack and/or scratch in the syringe) during the test process implemented by the test unit 7. The limits can be determined using averages of response parameters and/or statistical analysis including standard deviations.

The test unit 7 is programmable and/or configurable to test syringes to detect structural abnormalities of syringes. The test unit 7 can be programmed and/or configured to vibrate the transducer at one or more frequencies and to receive a response of a syringe to the vibrations using the receiver 4. The test unit 7 can be programmed and/or configured to identify response parameters including, for example, a peak amplitude of the response, a frequency at which the peak amplitude occurs, and/or a bandwidth of the response. Using the response parameters of one or more syringes, the test unit 7 can be programmed and/or configured to determine a structural characteristic of the syringe (e.g., whether there is a crack or scratch in the syringe). For example, the test unit 7 can be programmed and/or configured to compare the response parameters to a signature generated by the characterization unit 6 to determine whether one or more of the response parameters are within the limits defined in the signature. The test unit 7 can alert or otherwise notify an operator of a structural characteristic of the syringe (e.g., a crack or scratch).

In exemplary embodiments, the transducer 3 can be a piezo-electric device that vibrates at a frequency in response to a stimulus (e.g., electricity). In exemplary embodiments, the transducer 3 can be configured to emit ultrasonic radiation to generate acoustic vibrations in a syringe. Ultrasonic radiation generally encompasses a frequency range of about 20 kilohertz (kHz) to about 20 megahertz (MHz). In exemplary embodiments, the transducer 3 can be configured to vibrate at one or more frequencies in the ultrasonic frequency range. For example, the transducer 3 can be configured to vibrate at one or more frequencies between about 20 kHz and about 90 kHz and/or between about 25 kHz and about 50 kHz. The transducer 3 can be positioned proximate to the syringe and, in some embodiments, can be placed in physical contact with the syringe to propagate ultrasonic radiation through the syringe.

In exemplary embodiments, the receiver 4 can be a sensor, such as an acoustic sensor, configured to receive, detect, measure, and/or sense a response of the syringe to acoustic vibrations induced in the syringe by the output of the transducer 3. For example, the receiver 4 can be configured to measure acoustic vibrations in the form of ultrasonic radiation emanating from the syringe. In exemplary embodiments, the receiver can be positioned proximate to the barrel of the syringe and, in some embodiments, the sensor can be placed in physical contact with the barrel of the syringe. In some embodiments, a peak amplitude of the response to a resonance ultrasonic frequency associated with the syringe can be between about 30 kHz and 45 kHz and/or between about 33 kHz and 43 kHz.

In one exemplary embodiment, ultrasonic vibrations are induced in the syringe at a resonance frequency associated with the syringe and response parameters characterize a resonance ultrasonic vibration response including, for example, an amplitude, bandwidth, and peak position of the response. The amplitude or magnitude of the response can be plotted in a frequency scale to generate a resonant frequency response curve. In some embodiments, when there is a crack or scratch in the syringe, a reduction of the peak amplitude, a shift of the peak to a lower frequency, and/or an increase of the peak bandwidth can be detected and measured as compared to a like syringe with no cracks or scratches.

In some embodiments, a location at which the transducer 3 and/or receiver 4 are positioned with respect to the syringe can be varied such that the transducer 3 can stimulate the syringe at a different location and/or a response to the output of the transducer 3 can be detected, measured, or sensed at different locations on the syringe. In some embodiments, the location of the transducer 3 and/or receiver 4 can be fixed along a longitudinal axis L of the syringe 5. Additionally, as shown in phantom in FIG. 1, the system 1 can include multiple transducers 3 and/or multiple receivers 4 positioned at different locations along the longitudinal axis L of the syringe 5.

In some embodiments, the transducer 3 and/or receiver 4 can be moved towards and/or away from the body of the syringe 5 via adjustably positioned arms or stages 11, which can be pneumatically or otherwise controlled by the profiler 2. The stages 11 can have one or more degrees of freedom to permit movement along the longitudinal axis L of the syringe and/or radially about the syringe 5.

In one exemplary embodiment, as shown in FIG. 1, the transducer 3 and receiver 4 can be positioned at the same or substantially similar location along the longitudinal axis of the syringe, but can be radially offset from each other by about one hundred eighty degrees) (180°. In another exemplary embodiment, the transducer 3 and the receiver 4 can be positioned at different locations along the longitudinal axis of the syringe without being radially offset from one another (FIG. 3) or with a radial offset (FIG. 4).

Figure 2:
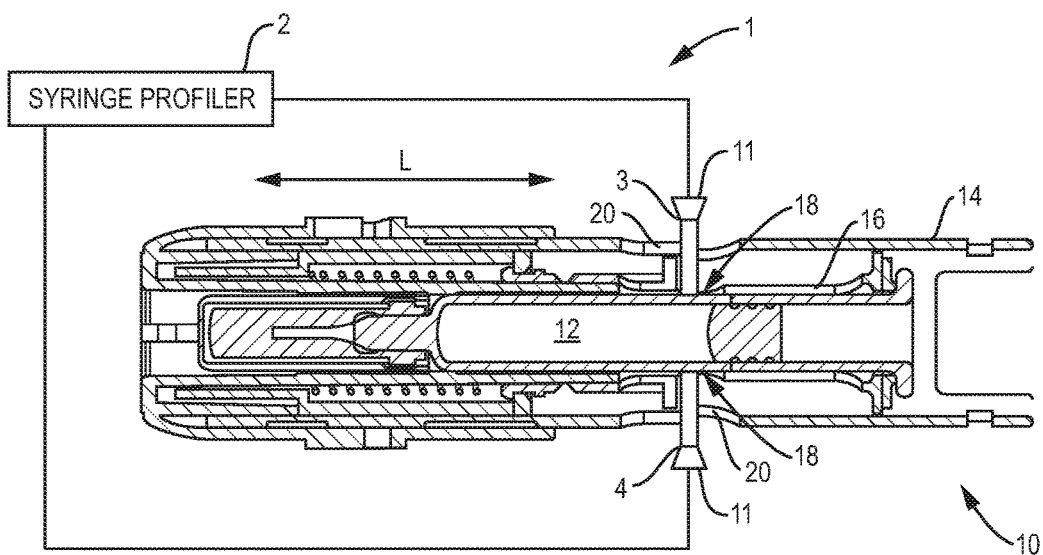
FIG. 2 illustrates an exemplary embodiment of a syringe characterization and testing system configured to determine a characteristic associated with a syringed incorporated into an exemplary automatic injection device.

FIG. 2 illustrates interfacing the system 1 with a syringe 12 that is housed in an automatic injection device 10. A cross-sectional view of a portion of the automatic injection device 10 is shown in FIG. 2. The automatic injection device 10 can include a syringe housing 14 and a syringe carrier 16. The syringe 12 rests in the syringe carrier 16, and both are contained in the syringe housing 14. The illustrative syringe housing 14, syringe 12, and syringe carrier 16 can have generally tubular structures. The syringe carrier and/or syringe housing can at least partially surround a circumference of the syringe.

The syringe carrier 16 can include window cutouts 18 preferably aligned with windows 20 formed on the housing 14. The cutouts 18 can be formed in an opposing relation such that a first one of the cutouts 18 is radially offset from a second one of the cutouts 18 by about one hundred eighty degrees (180°). Likewise, the windows 20 can be formed in an opposing relation such that a first one of the windows 20 aligns with the first one of the cutouts and is radially offset from a second one of the windows 20 by one hundred eighty degrees (180°) so that the second one of the windows 20 aligns with the second one of the cutouts 18. In exemplary embodiments, cutouts 18 and windows 20 can have a key-hole shape. In other exemplary embodiments, the cutouts 18 and windows 20 can have different shapes and/or can be disposed at different radial and/or longitudinal positions on the housing 14. For example, the cutouts 18 and/or windows 20 can be elongated slots extending along a longitudinal axis of the syringe such that a larger portion of the syringe is viewable and/or accessible through the windows 20 and cutouts 18. Structural features of exemplary automatic injection devices of the present disclosure are described in more detail below with respect to FIGS. 13-15 as well as in co-pending U.S. patent application Ser. No. 12/074,704 filed on Mar. 5, 2008, the disclosure of which is incorporated herein by reference in its entirety.

In exemplary embodiments, the windows 20 and the cutouts 18 can provide unobstructed access and/or visibility to a portion of the syringe 12. The transducer 3 and receiver 4 can be placed proximate to and/or in physical contact with exposed portions the syringe 12 accessible via the windows 20 and cutouts 18 to facilitate characterization and/or detection of structural characteristics of the syringe 12 (e.g., cracks and/or scratches). For example, the transducer 3 can be adjustably positioned to extend through one of the windows 20 and the corresponding one of the cutouts 18 by one of the adjustable stages 11 so that the transducer 3 contacts the body of the syringe. Likewise, the receiver 4 can be adjustably positioned to extend through one of the windows 20 and the corresponding one of the cutouts 18 by one of the adjustable stages 11 so that the receiver 4 contacts the body of the syringe 12. In some embodiments, the transducer 3 and receiver 4 can be positioned proximate to and/or in physical contact with other portions of the of the automatic injection device 10 including, for example, on the surface of the housing or other components of the device 10.

Figure 5:
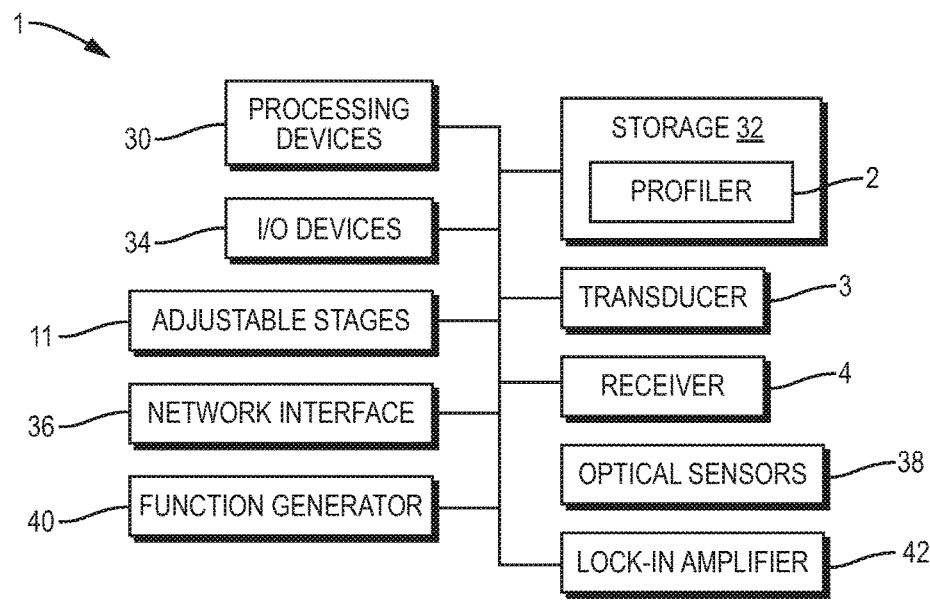
FIG. 5 is an exemplary embodiment of the syringe characterization and testing system implemented using a customized computing device.
Figure 8:
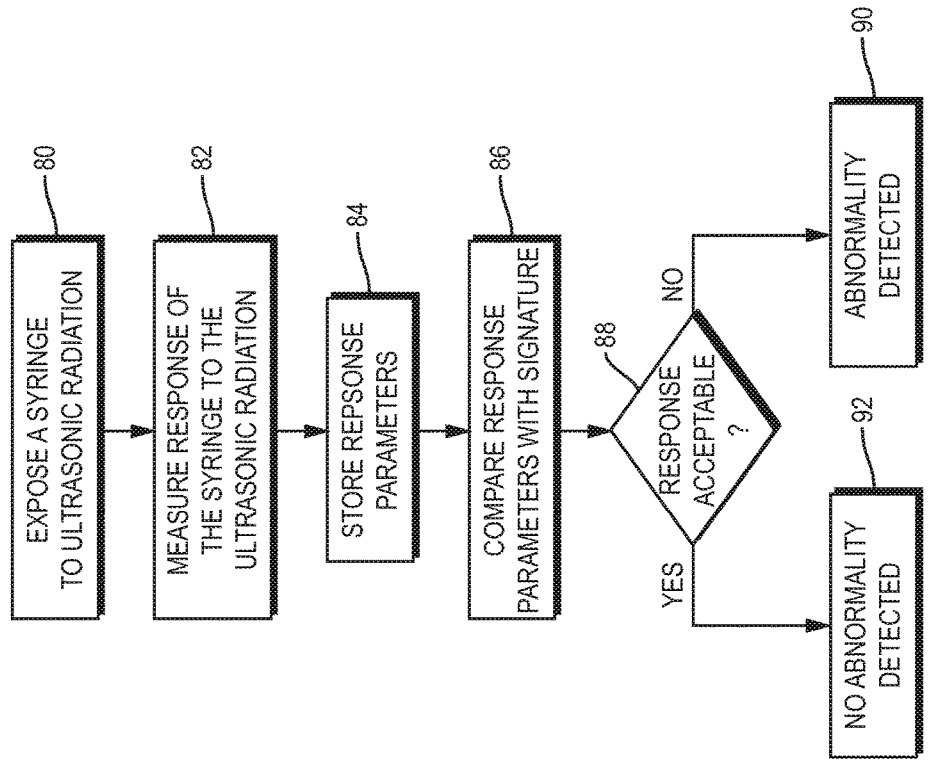
FIG. 8 is a flowchart illustrating an exemplary syringe testing procedure.
Figure 7:
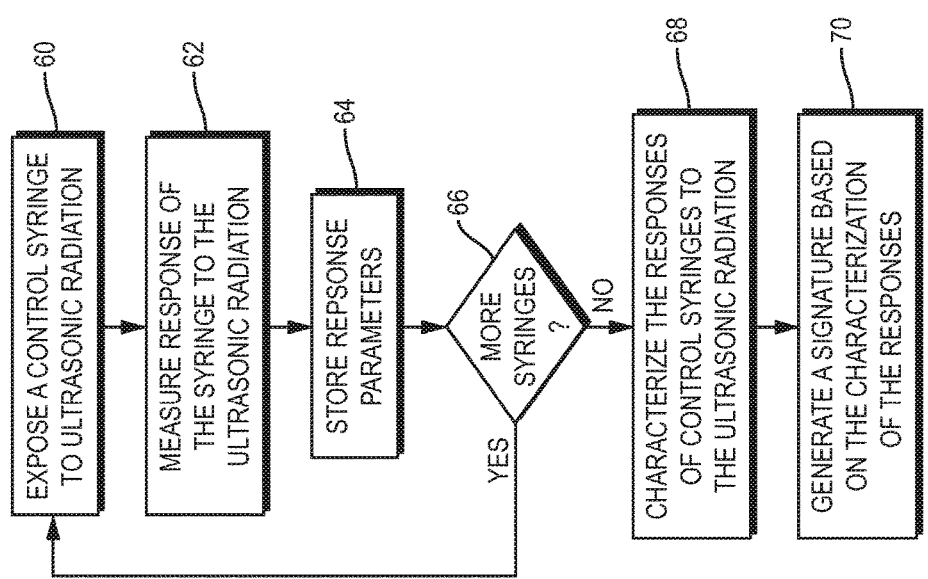
FIG. 7 is a flowchart illustrating an exemplary syringe characterization process.

FIG. 5 is a block diagram of an exemplary embodiment of the system 1 implemented using a customized computing device programmed and/or configured to perform the operational functions depicted, for example, in FIGS. 7 and 8. In the illustrated embodiment, the system 1 includes one or more programmable and/or configurable processing devices 30, such as a processor and/or controller, operatively coupled to storage 32. The processing device 30 can further be operatively coupled to input/output devices 34, such as a display device, keyboard, touch screen, mouse, printer, and the like, and can be operatively coupled to a network interface 36 to facilitate communication between the system 1 and other devices communicative coupled to a network.

Additionally, the programmable and/or configurable processing device 30 can be operatively coupled to the transducer 3, receiver 4, stages 11, and an optical sensor 38. The optical sensor 38 can be used by the system 1 to determine whether a syringe is properly aligned in a receiving area (not shown) of the system 1 to permit interaction of the syringe with the system 1. The receiving area provides an area for receiving syringes (e.g., standalone syringes and/or syringes incorporated in an automatic injection device). In exemplary embodiments, the receiving area can be configured to adjust the position of the syringe in the cabinet and can be configured to adjust the position of the syringe with respect to the receiving area by, for example, rotating the syringe about a center axis of the syringe.

The storage 32 stores data and instructions and can be implemented using non-transitory computer readable medium technologies, such as a floppy drive, hard drive, tape drive, solid state storage devices, Flash drive, optical drive, read only memory (ROM), random access memory (RAM), and the like. Applications, such as an embodiment of the profiler 2, or portions thereof, can be resident in the storage 32 and can include instructions for implementing the applications. The processing device 30 operates to execute the applications in storage 32, such as the profiler 2, by executing instructions therein. Data resulting from the executed instructions can be stored in storage 32 and/or can be presented on a display via, for example, a graphical user interface (GUI).

In some embodiments, the system 1 can include a programmable function generator 40 that may be controlled by one or more of the processing devices to output a time varying signal to the transducer to control the amplitude and frequency of the vibration output by the transducer 3. In some embodiments, the output of the receiver 4 can pass through a lock-in amplifier 42 to aid in measuring the response. The lock-in amplifier 1064 can be configured to maintain detection of the frequency (i.e., lock-in on the frequency) at which the syringe vibrates. In some embodiments, at least one of the one or more processing devices 30 can include a programmable logic controller to control various operations of the adjustable stages 11 to position the transducer 3 and/or receiver 4, and/or to adjust the position of the receiving area.

Figure 6:
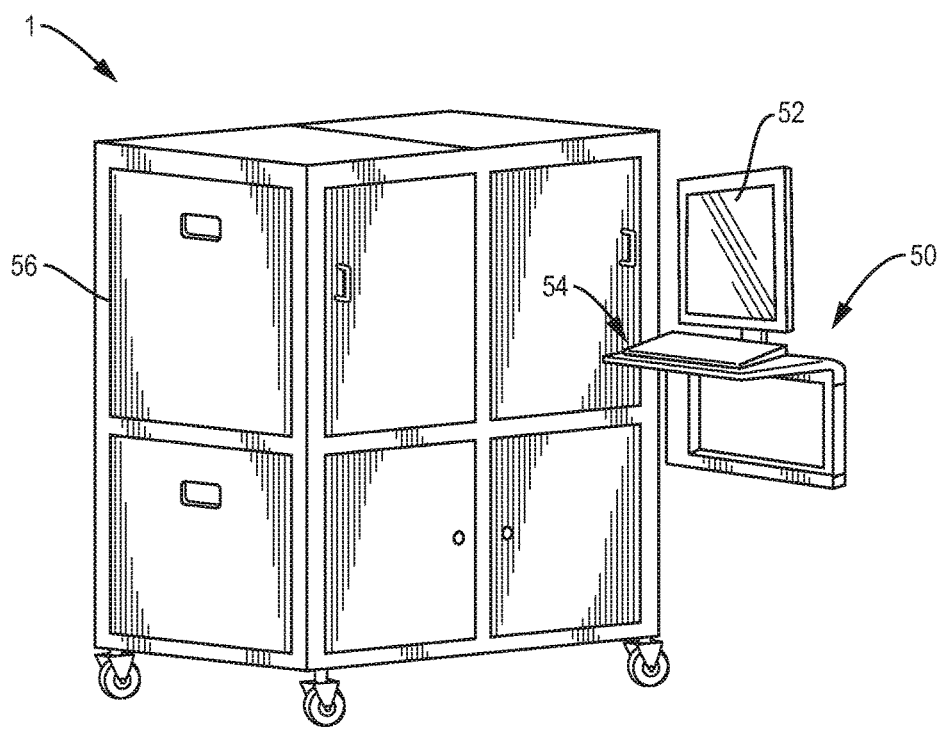
FIG. 6 is another exemplary embodiment of the syringe characterization and testing system implemented using a customized computing device and a cabinet.

In another exemplary embodiment, as shown in FIG. 6, the system 1 can be implemented using a computing device 50 and a cabinet 56. The computing device 50 can be a configured to include the profiler 2 and can have a display 52 and a user interface 54, such as a keyboard and mouse. The cabinet 56 can house the adjustable stages, transducer, and receiver, each of which can be in communication with the computing device 50. While FIG. 6 has been illustrated using a cabinet, those skilled in the art will recognize that the system 1 can be implemented in different environments. For example, the system can be implemented as a bench-top system, an assembly or manufacturing line component, or in any other environment.

FIG. 7 is a flowchart illustrating an exemplary syringe characterization process. In the exemplary syringe characterization process, one or more like syringes are characterized to determine a signature associated with like syringes having like conditions (e.g., substantially identical syringes without cracks or scratches). To begin, a control syringe (e.g., a normal standalone syringe or a normal syringe incorporated in an automatic injection device) can be placed in a receiving area of the system and can be aligned to permit the transducer and receiver to be positioned proximate to the syringe. In some embodiments, the syringe can be filled with a therapeutic agent. In some embodiments, the transducer and/or receiver can be moved into place using one of the adjustable stages so that the transducer is proximate to and/or in physical contact with the syringe. In some embodiments, once the control syringe is placed in the receiving area and aligned thereto, the transducer and/or receiver can be in appropriate positions to facilitate characterization.

The control syringe is exposed to ultrasonic radiation via the transducer of the system (step 60). An acoustic response of the syringe is measured using the receiver (step 62) and the parameters of the response are stored (step 64). If there are more syringes to be used for the characterization process (step 66), the additional syringes are exposed to the ultrasonic radiation (step 60) and their responses are measured (step 62) and stored (step 64). If no additional syringes are being used for the characterization (step 66), the characterization process characterizes the responses of the control syringes to the ultrasonic radiation (step 68). Using the characterization of the responses, the system automatically computes a signature for the syringes (step 70).

The signature can be associated with syringe attributes for the control syringes so that the signature can be used for subsequent testing of syringes having substantially similar syringe attributes. In exemplary embodiments, the signature generated using the characterization process can average the responses and/or perform statistical calculations to determine acceptable responses of syringes having substantially similar attributes to the characterized syringes. For example, the signature can include upper and/or lower limits corresponding to a peak amplitude of the response, a bandwidth of the response, and/or a frequency of the peak amplitude. The upper and/or lower limits can be based on, for example, one or more standard deviations for one or more of the response parameters.

FIG. 8 is a flowchart illustrating an exemplary syringe defect detection process. In an exemplary syringe testing process, one or more syringes are tested to determine whether a syringe defect exists. To begin, a syringe under test (e.g., a standalone syringe or a syringe incorporated in an automatic injection device) can be placed in a receiving area of the system and can be aligned to permit the transducer and receiver to be positioned proximate to the syringe. In some embodiments, the transducer and/or receiver can be moved into place using one of the adjustable stages so that the transducer is proximate to and/or in physical contact with the syringe. In some embodiments, once the syringe is placed in the receiving area and aligned thereto, the transducer and/or receiver can be in appropriate positions to facilitate testing of the syringe under test for structural abnormalities.

To begin, a syringe under test is exposed to ultrasonic radiation via the transducer of the system (step 80). The frequency and/or amplitude of the ultrasonic radiation can be based on the syringe attributes associated with the syringe under test and/or syringe characterization results. An acoustic response of the syringe is measured (step 82) using the receiver and the response parameters are stored (step 84). The response parameters can be compared to the signature generated for control syringes having identical or substantially identical syringe attributes (step 86). If the response is not acceptable (step 88), the syringe is identified as having a structural characteristic associated with a structural abnormality, such as a crack or scratch (step 90). Otherwise, the syringe is identified as having a structural characteristic associated with no detection of structural abnormalities (step 92).

Exemplary embodiments provide a non-destructive, efficient, and effective approach to detecting unacceptable structural abnormalities in syringes using acoustic vibrations or detecting acceptable syringes. For example, by inducing acoustic vibrations in a syringe and measuring the response, structural abnormalities can be detected that may not be visibly or optically detected. Furthermore, exemplary embodiments of the present disclosure permit detection of structural abnormalities when syringes are incorporated into automatic injection devices and only a small portion of the syringe in an automatic injection device may be visible/accessible.

Experiments were performed on standalone syringes as well as syringes incorporated in an automatic injection device to determine whether acoustic vibrations provide an effective approach to detecting structural abnormalities in standalone syringes and syringes incorporated in automatic injection devices. To simulate, real world conditions of pre-filled syringes, the syringes were filled with a volume of water. The experiments were performed to determine whether the syringes would have a meaningful response to ultrasonic radiation given the geometry of the syringes (i.e., cylindrical) and the response dampening effects of being filled with a fluid and/or housed in an automatic injection device.

With respect to the standalone syringes an acoustic response over a wide frequency range was measured, and the most prominent resonant ultrasonic vibration peak was selected, which occurred close to about 38.5 kHz. The frequency response of the ultrasonic transducer and receiver is generally flat in the range of about 38.5 kHz peak. The characteristics of 38.5 kHz peak were analyzed on a set of normal and scratched syringes. Each set contained ten (10) samples. Every syringe was measured five (5) times to accommodate an effect of manual positioning.

Average data were analyzed and are presented in Tables 1 and 2 for normal and scratched syringes, respectively. Table 1 lists measured responses to induced vibration in normal standalone syringes (i.e., syringe without structural abnormalities) using the transducer. Table 2 lists measured responses to induced vibrations in standalone syringes with known structural abnormalities) using the transducer. Tables 1 and 2 include measured peak amplitudes, peak frequencies, and response bandwidths for the sample syringes.

Figure 9A:
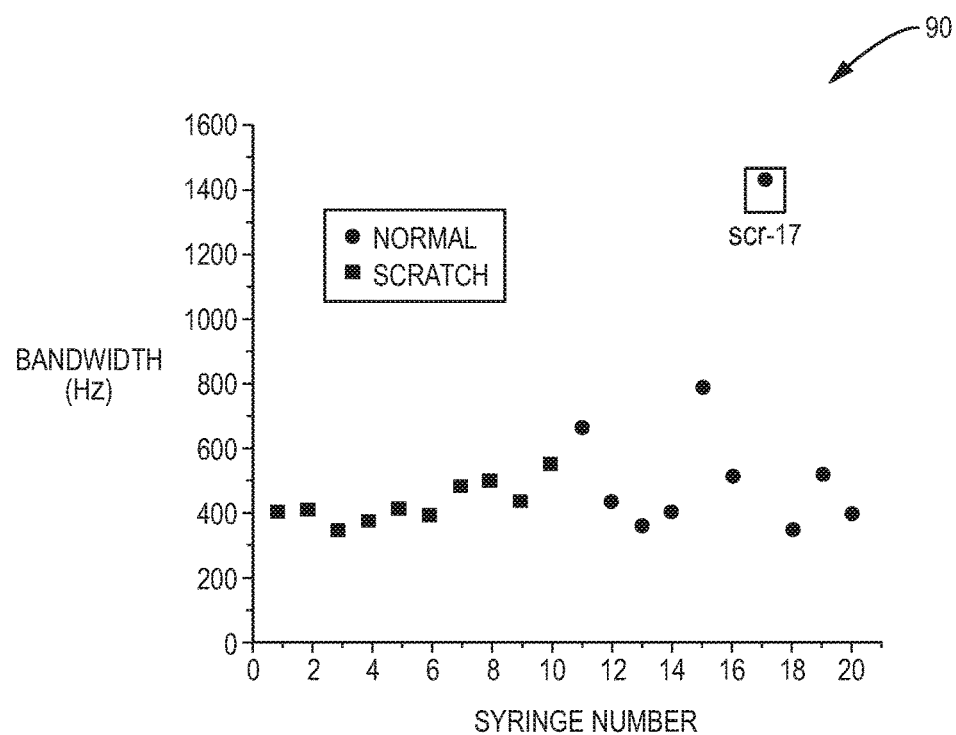
FIG. 9a illustrates experimental results for standalone syringes in which a bandwidth of the responses to resonant ultrasonic vibrations is measured for syringes numbered 1-20 in Tables 1 and 2.
Figure 9B:
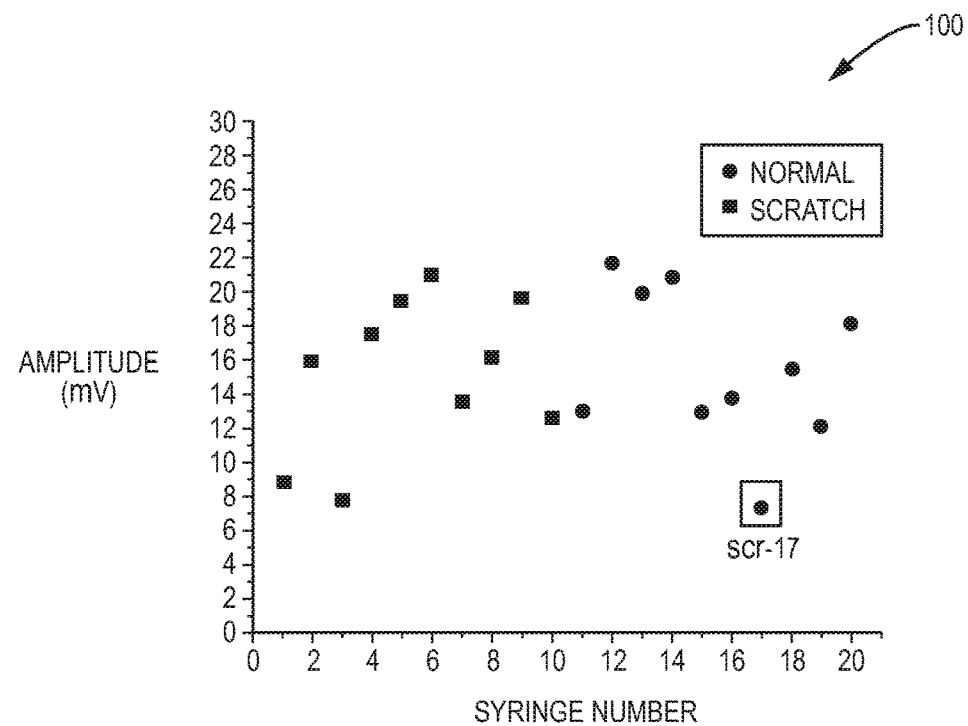
FIG. 9b illustrates experimental results for standalone syringes in which an amplitude of the responses to resonant ultrasonic vibrations is measured for syringes numbered 1-20 in Tables 1 and 2.
Figure 9C:
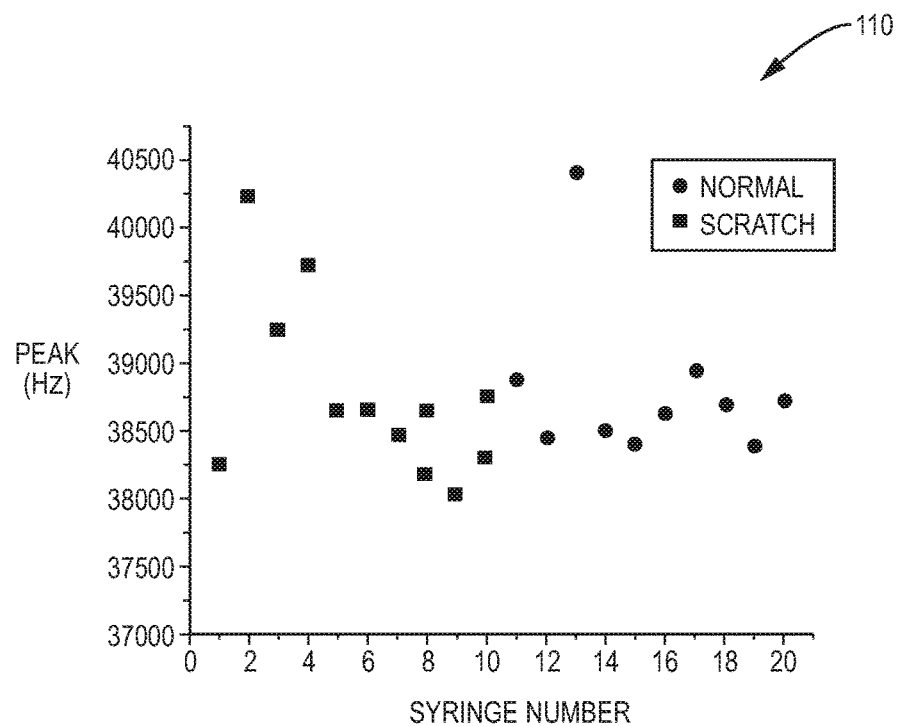
FIG. 9c illustrates experimental results for standalone syringes in which a peak frequency of the responses to resonant ultrasonic vibrations is measured for syringes numbered 1-20 in Tables 1 and 2.

Based on the data included in Tables 1 and 2 it was observed that the bandwidth on some scratched syringes was far above the average value and the standard deviation for the bandwidth. Examples are represented by samples Scr-11, Scr-15, and Scr-17. The Scr-17 sample is statistically rejected based on large value of bandwidth and low amplitude using statistical software developed. FIG. 9a is a plot 90 of the bandwidth of the syringe samples using the data from Tables 1 and 2, FIG. 9b is a plot 100 of the peak amplitude of the response for the syringe samples using the data from Tables 1 and 2, and FIG. 9c is a plot 110 of the peak frequency of the response using the data from Tables 1 and 2.

TABLE 1

Response Parameters for a set of ten normal standalone syringes

| Sample ID | Amplitude [mV] | Peak [Hz] | Bandwidth [Hz] |
|---|---|---|---|
| Nor-1 | 8.8 | 38253.0 | 405.3 |
| Nor-2 | 15.8 | 40222.2 | 409.4 |
| Nor-3 | 7.7 | 39247.0 | 351.6 |
| Nor-4 | 17.5 | 39727.6 | 377.0 |
| Nor-5 | 19.4 | 38650.2 | 417.2 |
| Nor-6 | 20.9 | 38622.8 | 483.2 |
| Nor-7 | 13.6 | 38472.0 | 503.8 |
| Nor-8 | 16.2 | 38652.4 | 503.8 |
| Nor-9 | 19.8 | 38030.0 | 436.6 |
| Nor-10 | 12.6 | 38753.8 | 554.8 |
| Average | 15.2 | 38867.1 | 433.7 |
| Stand Dev. | 4.5 | 675.2 | 62.1 |

TABLE 2

Response Parameters for a set of ten standalone syringes having structural abnormalities

| Sample ID | Amplitude [mV] | Peak [Hz] | Bandwidth [Hz] |
|---|---|---|---|
| Scr-11 | 13.0 | 38873.6 | 670.6 |
| Scr-12 | 21.7 | 38443.2 | 438.0 |
| Scr-13 | 19.9 | 40411.2 | 363.6 |
| Scr-14 | 20.9 | 38513.0 | 407.0 |
| Scr-15 | 12.9 | 38402.2 | 795.6 |
| Scr-16 | 13.8 | 38632.4 | 519.2 |
| Scr-17 | 7.3 | 38943.6 | 1429.8 |
| Scr-18 | 15.5 | 38687.6 | 355.0 |
| Scr-19 | 12.1 | 38387.0 | 529.4 |
| Scr-20 | 18.1 | 38724.2 | 407.0 |
| Average | 15.5 | 38801.8 | 591.5 |
| Stand Dev. | 4.5 | 596.9 | 326.4 |

Figure 10A:
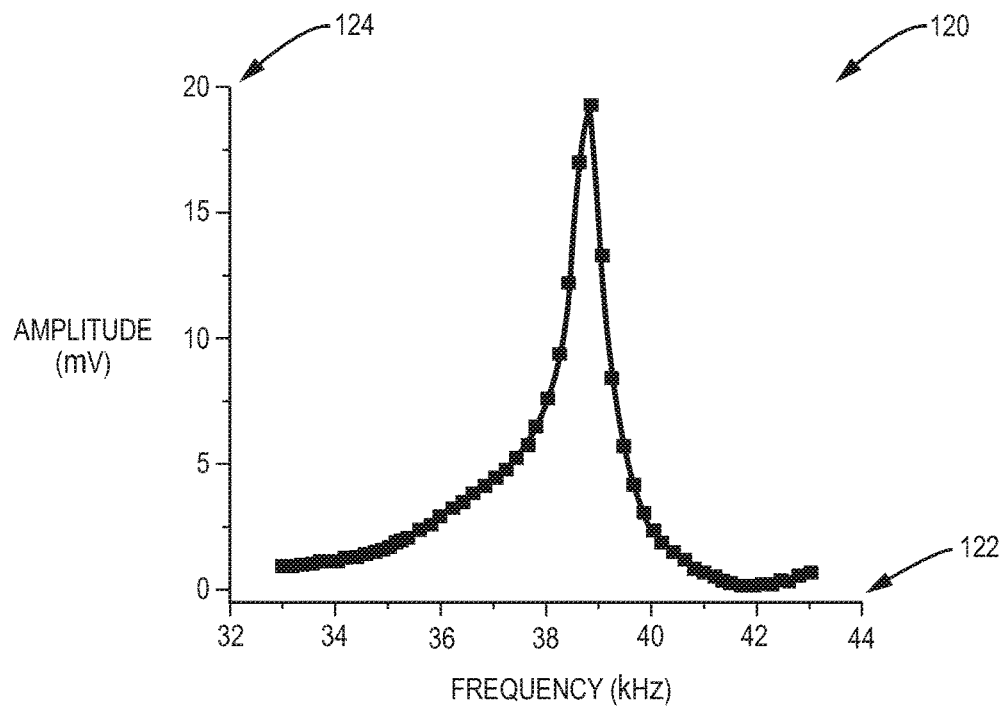
FIG. 10a illustrates a response curve of a syringe for different frequencies of vibrations induced in the syringe.
Figure 10B:
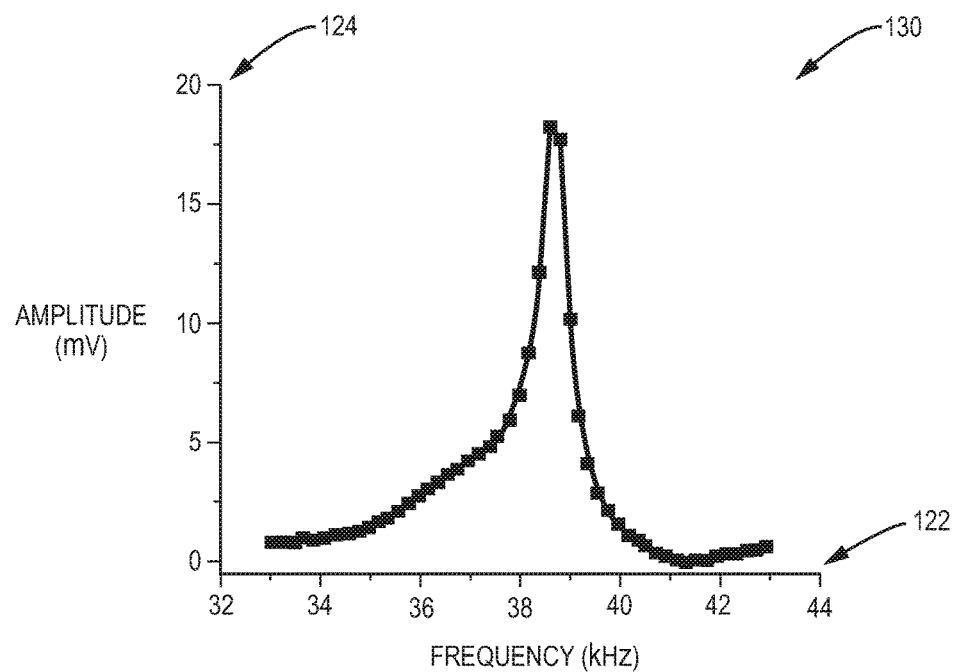
FIG. 10b illustrates a response curve of another syringe for different frequencies of vibrations induced in the syringe
Figure 10C:
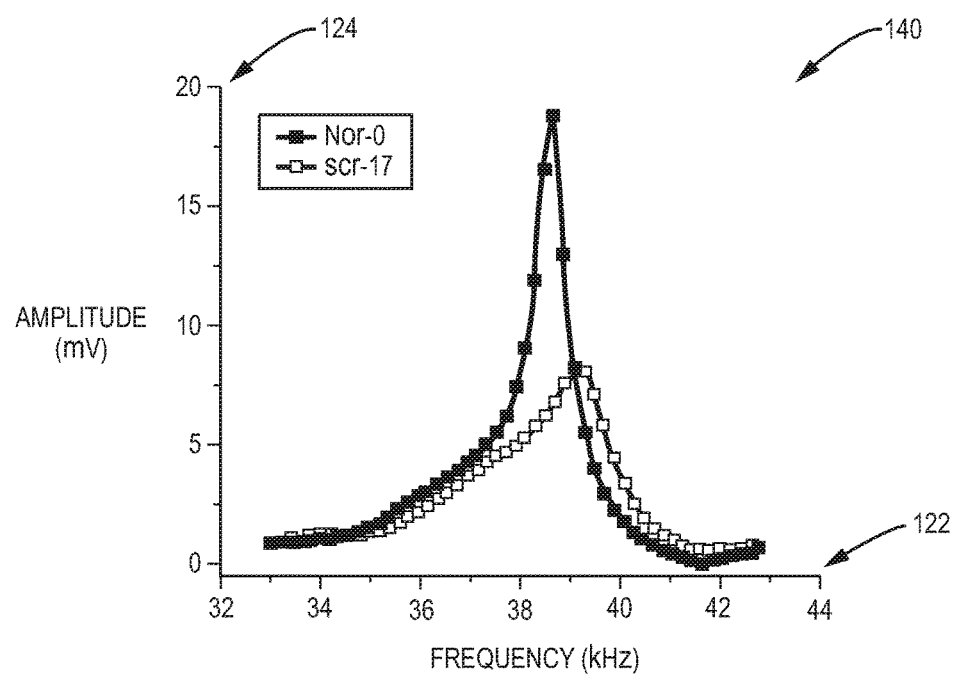
FIG. 10c illustrates a comparison of a response curve of a normal syringe and a syringe having a structural abnormality.

FIGS. 10a-b are graphs 120 and 130, respectively, of resonant response or frequency response curves illustrating typical resonance peaks measured for standalone syringes. FIG. 10c is a graph 140 of resonant response curves illustrating a comparison between a normal syringe, Nor-9, and a scratched syringe, Scr-17. The x-axis 122 of the graphs in FIGS. 10a-c corresponds to frequency in kilohertz (kHz) and the y-axis 124 of the graphs in FIGS. 10a-c corresponds to amplitude in millivolts (mV). As shown in FIG. 10c, the scratched syringe, Scr-17 has a lower peak amplitude than a normal syringe, a larger bandwidth than a normal syringe, and a different peak frequency than the normal syringe.

Figure 11:
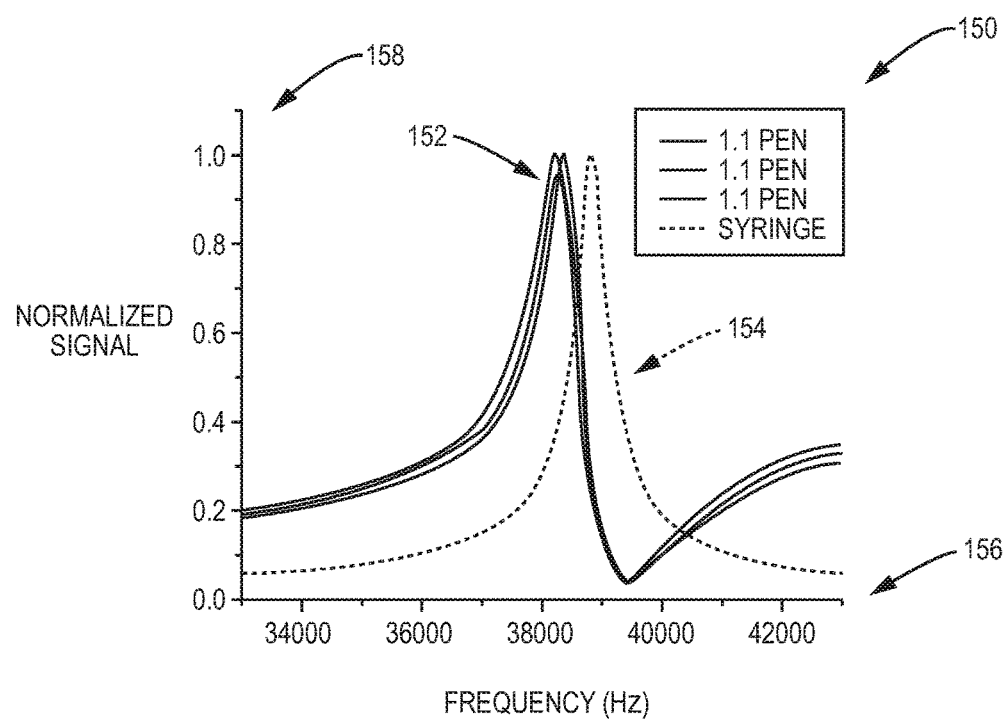
FIG. 11 illustrates a comparison of between response curves for a bare syringe and a syringe incorporated or encased in an automatic injection device.

FIG. 11 is a graph 150 that illustrates an exemplary frequency response 152 of a syringe in an automatic injection device compared to a frequency 154 of a standalone syringe. The x-axis 156 of the graphs in FIG. 11 corresponds to frequency in kilohertz (kHz) and the y-axis 158 of the graph 150 in FIG. 11 corresponds to amplitude in millivolts (mV). Three (3) scans of the syringe in the automatic injection device are plotted to evaluate a variation of the peak parameters. In comparison to the peak parameters for the standalone syringe, the peak amplitude is lower (1.5 mV), the bandwidth is larger, and there is a frequency shift in the peak. The parameter shifts are attributed to the influence of the automatic injection device, which at least partially dampens the resonance of the syringe. The peak of the response is well defined and located in a similar frequency range as the standalone syringe (e.g., about 38 KHz).

Figure 12:
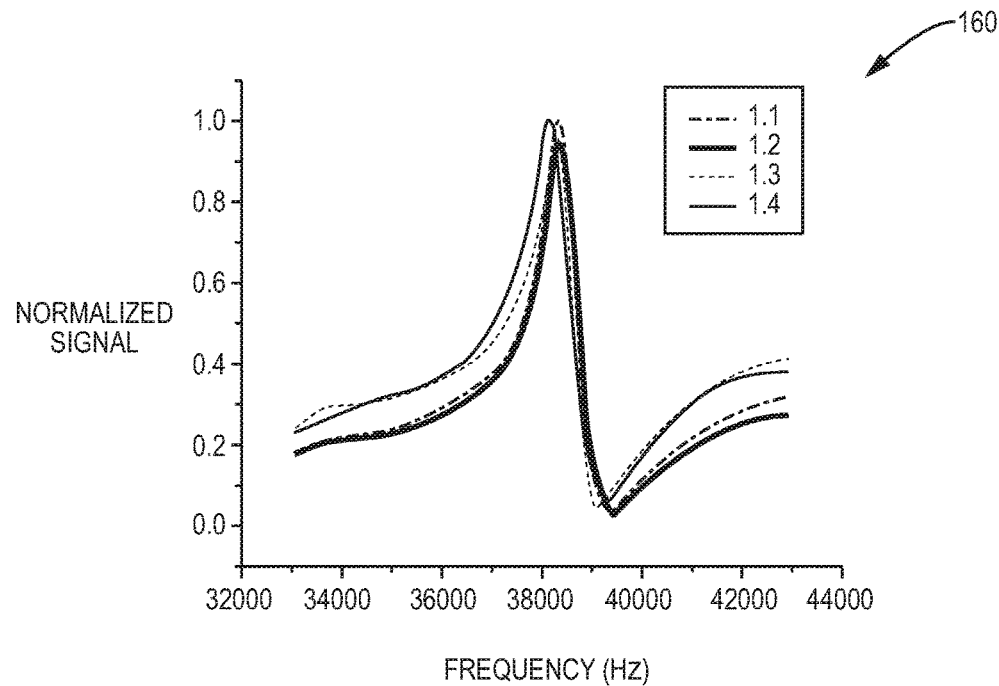
FIG. 12 illustrates a normalized plot of response curves for syringes of automatic injection device.

FIG. 12 shows a graph 160 of resonant response or frequency response curves for four automatic injection device assemblies. Each device assembly response was measured three (3) times, normalized with respect to amplitude, and average values plotted. A high variation between individual scan amplitudes was detected, therefore the data is normalized to the maximum value. This variability can be reduced using higher precision ultrasonic elements and pneumatic moving stages. As shown in FIG. 12, sample 1.4 has the largest scratching as determined, at least in part by its shift of approximately 380 Hz.

As a proof of concept further experiments were performed on syringes incorporated into an automatic injection device. The syringes were divided into good syringes (i.e., syringes without visible cracks) and cracked syringes.

The set of cracked syringes included two (2) water-filled syringes, assembled into auto injection devices. A response of each cracked syringe in the automatic injection device to ultrasonic vibrations was measured ten (10) times at 0 and 180 degrees (i.e. rotated radially about the center axis with respect to the transducer and sensor).

The set of good syringes included four (4) water-filled syringes, assembled into auto injection devices. A response of each good syringe in the automatic injection device to ultrasonic vibrations was measured 10 times at 0 and 180 degrees (i.e. rotated radially about the center axis with respect to the transducer and sensor).

Figure 13:
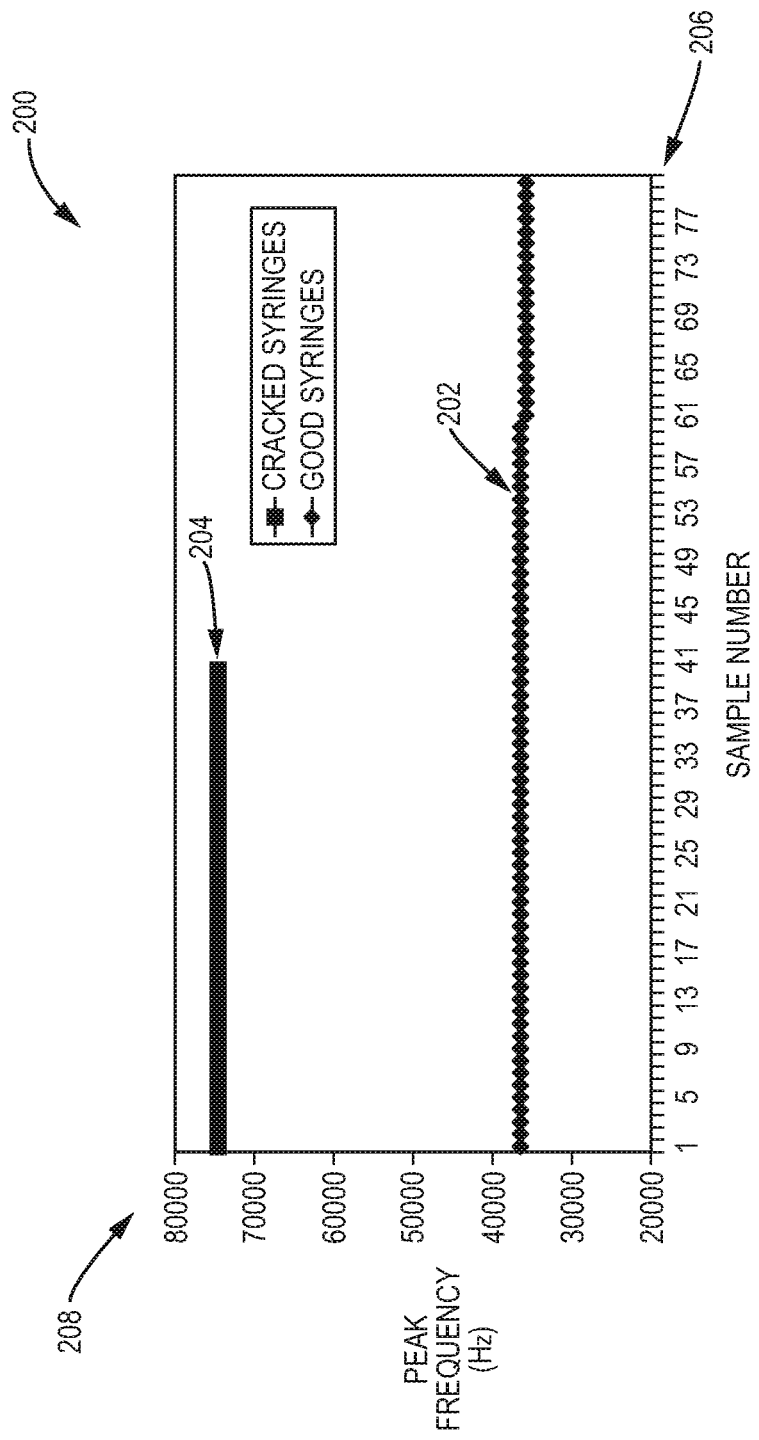
FIG. 13 is a graph that illustrates a comparison of a frequency response between good syringes and cracked syringes incorporated into an autoinjector device.

FIG. 13 depicts a graph 200 comparing a frequency response of the good syringes 202 to a frequency response of the cracked syringes 204. The x-axis 206 of the graph 200 corresponds to a sample test number and the y-axis 208 corresponds to a peak frequency in Hertz (Hz). As shown in the graph 200, the good syringes 202 in the automatic injection device had a peak frequency of about thirty-eight kilohertz (38 kHz) and the cracked syringes 204 in the automatic injection device has a frequency response of about seventy-five kilohertz (75 kHz).

Figure 14:
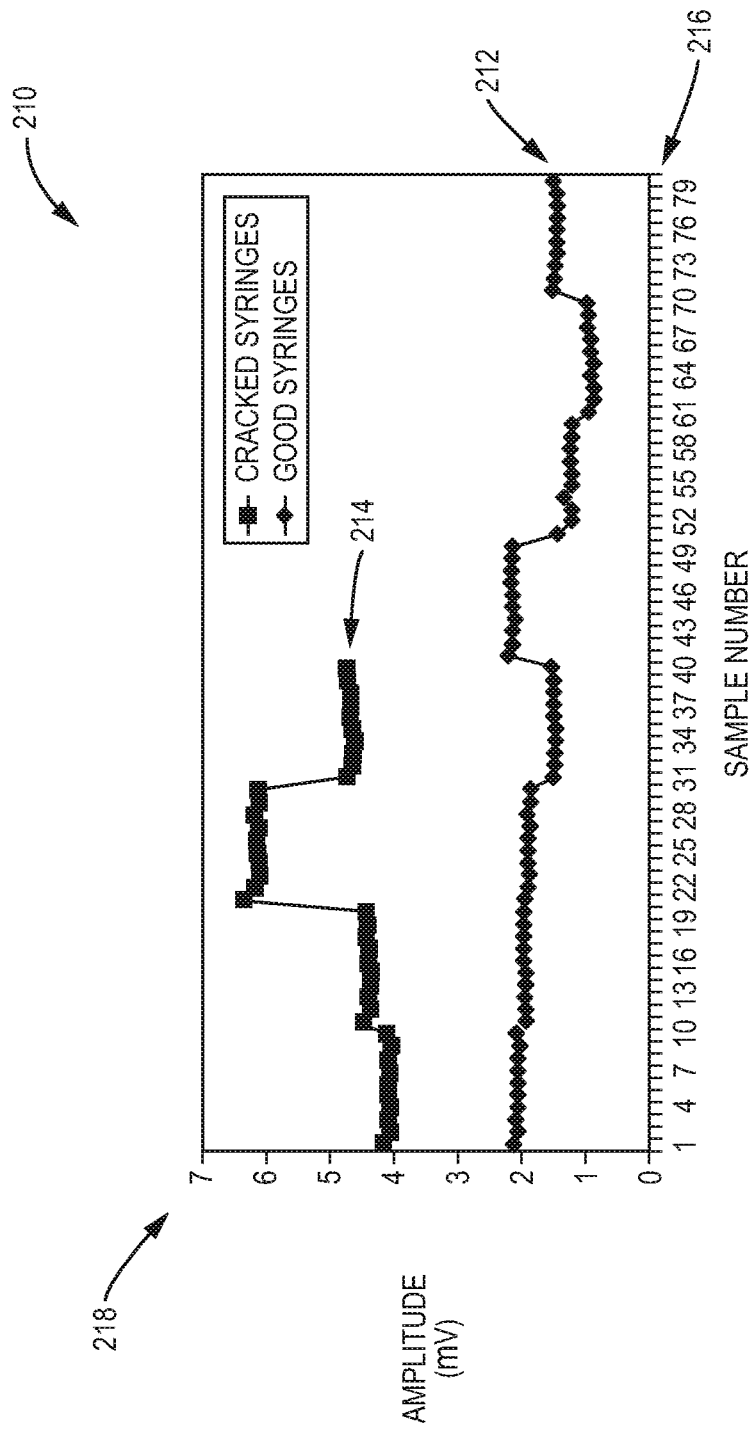
FIG. 14 is a graph that illustrates a comparison of an amplitude response between good syringes and cracked syringes incorporated into an autoinjector device.

FIG. 14 depicts a graph 210 comparing a peak amplitude of the response of the good syringes 212 to a peak amplitude of the response of the cracked syringes 214. The x-axis 216 of the graph 210 corresponds to a sample test number and the y-axis 218 corresponds to a response signal amplitude in millivolts (mV). As shown in the graph 210, the good syringes 212 in the automatic injection device have a measured signal amplitude of between about one and two millivolts (1-2 mV) and the cracked syringes 214 in the automatic injection device have a measured signal amplitude of between about four and six millivolts (4-6 mV).

Figure 15:
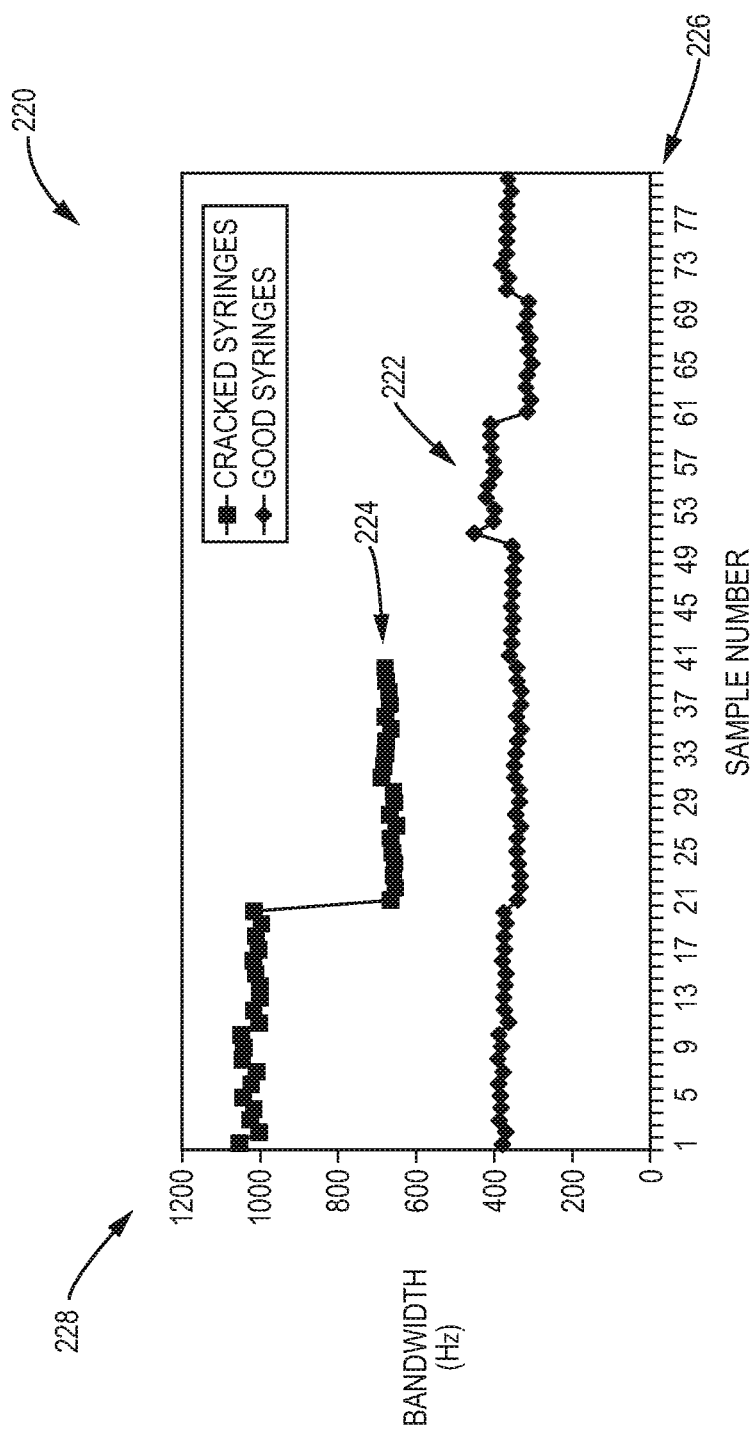
FIG. 15 is a graph that illustrates a comparison of a bandwidth response between good syringes and cracked syringes incorporated into an autoinjector device.

FIG. 15 depicts a graph 220 comparing a bandwidth of the response of the good syringes 222 to a bandwidth of the response of the cracked syringes 224. The x-axis 226 of the graph 220 corresponds to a sample test number and the y-axis 228 corresponds to a bandwidth in Hertz (Hz). As shown in the graph 220, the good syringes 222 in the automatic injection device have a measured bandwidth of between about three hundred and four hundred Hertz (300-400 Hz) and the cracked syringes 224 in the automatic injection device have a measured bandwidth of between about six hundred and one thousand Hertz (600-1000 Hz).

Exemplary Automatic Injection Devices

Automatic injection devices suitable for use with embodiments of the system 1 are described below relative to certain illustrative embodiments. While the automatic injection devices are described with respect to certain illustrative embodiments, those skilled in the art will recognize that the automatic injection devices of the present disclosure are not meant to be limiting and that other automatic injection devices can be suitable for use with embodiments of the system 1. In addition, the components and the method of using the automatic injection device are not limited to the exemplary embodiments described herein.

Figure 17:
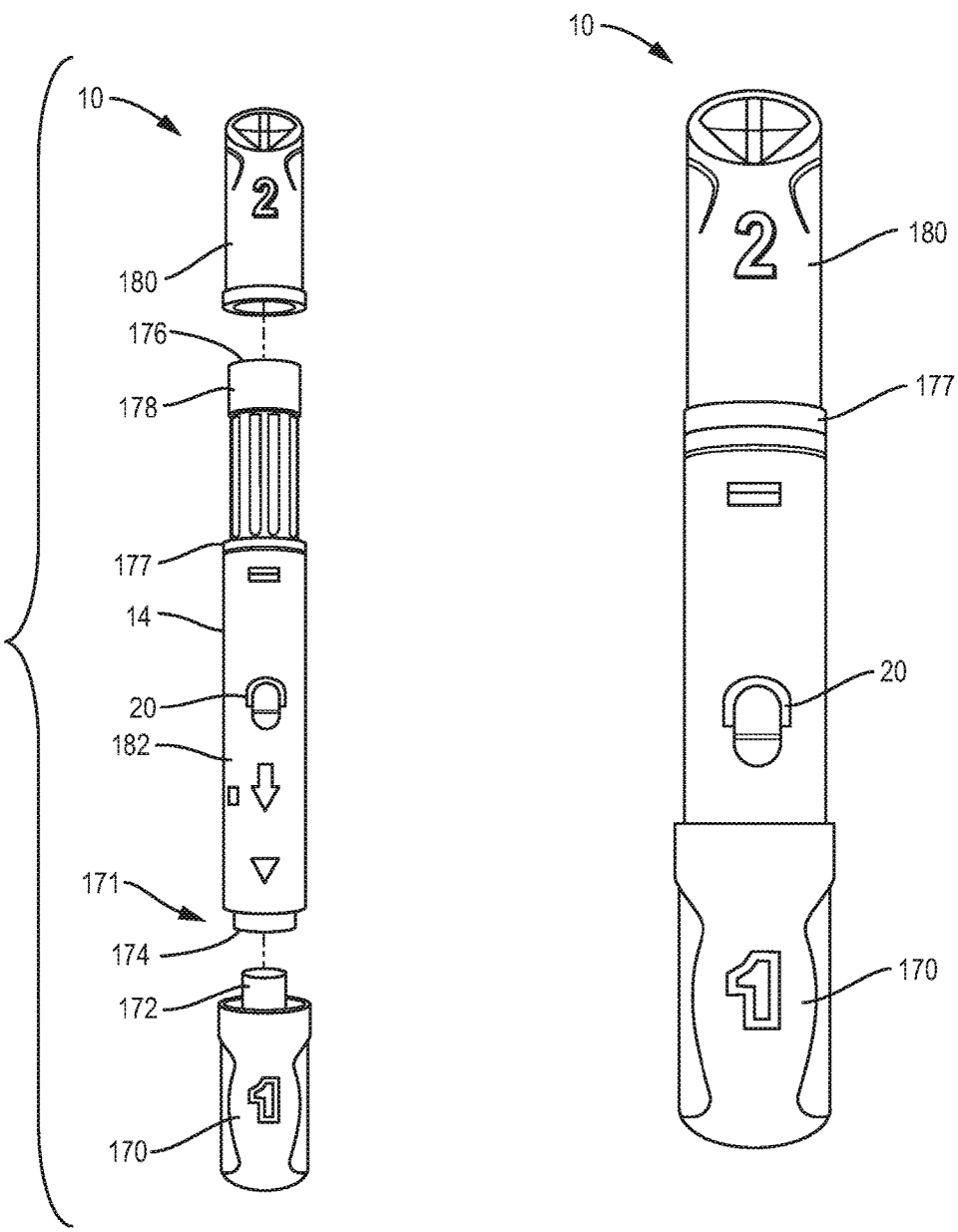
FIG. 17 illustrates a perspective view of the exemplary automatic injection device of FIG. 13 in which the housing is capped.

FIGS. 16 and 17 illustrate an exemplary automatic injection device 10 suitable for injecting a dose of a substance, such as a liquid drug, into a patient. FIG. 16 illustrates a perspective view of the exemplary automatic injection device 10 in which caps that cover proximal and distal ends of the housing are removed. FIG. 17 illustrates a perspective view of the exemplary automatic injection device 10 of FIG. 16 in which the proximal and distal ends of the housing are capped.

Referring to FIG. 16, the automatic injection device 10 includes a housing 14 for housing a container, such as a syringe, containing a dose of a substance to be injected into a patient's body. The housing 14 preferably has a tubular configuration, although one of ordinary skill in the art will recognize that the housing 14 may have any suitable size, shape and configuration for housing a syringe or other container. While exemplary embodiments will be described with respect to a syringe mounted in the housing 14, one of ordinary skill in the art will recognize that the automatic injection device 10 may employ any suitable container for storing and dispensing a substance.

The exemplary syringe is preferably slidably mounted in the housing 14, as described in detail below. When the device is in an inactivated position, the syringe is sheathed and retracted within the housing 14. When the device 10 is actuated, a needle of the syringe projects from a distal first end 171 of the housing 14 to allow ejection of the substance from the syringe into the patient's body. As shown, the distal first end 171 of the housing 14 includes an opening 174 through which the needle of the syringe projects during actuation of the device 10.

Referring still to FIG. 16, a proximal second end 176 of the housing 14 includes a firing engagement mechanism, e.g., a firing button 178, for actuating a firing mechanism. The housing 14 also houses the firing mechanism, e.g., one or more actuators, that moves the syringe from a sheathed position with the housing 14 to a projecting position and subsequently expels the substance from the syringe into the patient's body.

The exemplary automatic injection device 10 may also include a first removable cap 170 (or needle cap) for covering the first end 171 of the housing 14 to prevent exposure of the needle prior to an injection. In the illustrative embodiment, the first cap 170 may include a boss 172 for locking and/or joining the cap 170 of the device 10 until the patient is ready to activate the device 10. Alternatively, the first cap 170 may include a threaded screw portion, and the internal surface of the housing 14 at opening 174 may include a screw thread. Any suitable mating mechanism may be used in accordance with the teachings of exemplary embodiments.

The housing 14 and caps 170, 180 may further include graphics, symbols and/or numbers to facilitate use of the automatic injection device 10. For example, the housing 14 includes an arrow 182 on an outer surface pointing towards the first end 171 of the device 10 to indicate how the device 10 should be held relative to the patient (i.e., with the first end 171 adjacent to the injection site), as shown in FIG. 17. In addition, the first cap 170 is labeled with a "1" to indicate that a patient should remove the first cap 170 of the device first, and the second cap is labeled with a "2" to indicate that the second cap 180 should be removed after the first cap 170 is removed during preparation for and subsequent injection using the illustrative automatic injection device 10. One of ordinary skill in the art will recognize that the automatic injection device 10 may have any suitable graphics, symbols and/or numbers to facilitate patient instruction, or the automatic injection device may omit such graphics, symbols and/or numbers.

As shown in FIG. 17, the first end 171 of the housing 14 may have a wider diameter than the second end 176. A step 177 may be formed at the transition between the two diameters to accommodate the second cap 180 and to facilitate seating of the second cap 180 on the second end 176 of the housing.

The housing 14 may also preferably include display windows 20, at least one of which is obstructed in the present view, to allow the transducer and/or receiver of embodiments of the system 1 to be positioned proximate to the syringe 12 and to allow a patient to view the contents of the syringe housed within the housing 14. The windows 20 may include an opening in the sidewall of the housing 14, or may include a translucent material in the housing 14 to allow viewing of the interior of the device 10. For embodiments in which the windows 20 include openings, the transducer and/or receiver can be positioned to pass through the openings to be proximate to, and in some embodiments, in physical contact with the syringe 12.

The housing 14 may be formed of any suitable surgical material including, but not limited to, plastic and other known materials.

Figure 18:
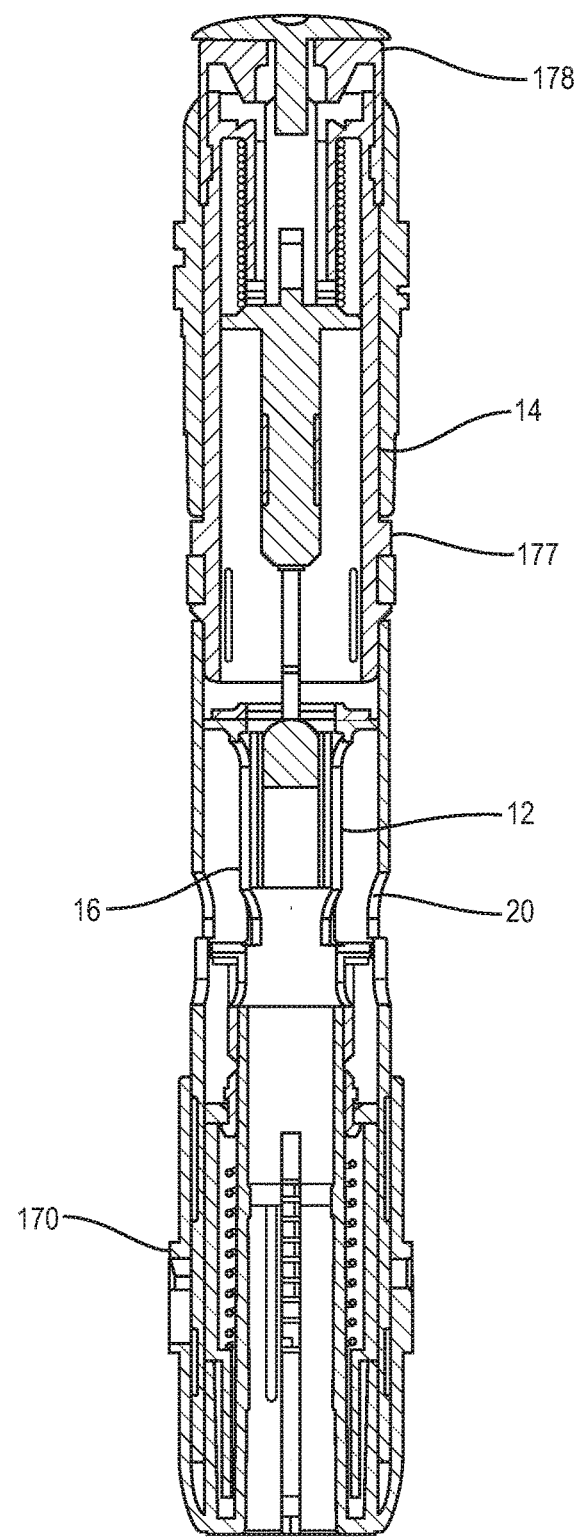
FIG. 18 illustrates a cross-sectional view of an exemplary assembled automatic injection device in accordance with exemplary embodiments.

FIG. 18 illustrates an assembled automatic injection device 10, wherein a syringe housing assembly 121 and a firing mechanism assembly 122 are coupled together, such that a pressurizer 754' of the syringe actuation component 700' extends into the barrel portion 53 of a syringe 12 housed in the syringe housing assembly 121 and in communication with a bung 54 of the syringe 12. A syringe carrier 16 of the illustrative embodiment envelopes the proximal half of a syringe 12 used in the device 10. The syringe 12 rests in the carrier 16 and both are contained in the housing 14. The housing 14 stops and limits the movement of the carrier 16, and the carrier 16 in turn stops and limits the movement of the syringe 12. The illustrative syringe carrier 16 has a substantially tubular structure including window cutouts 18 preferably aligned with the window 20 on the housing 14 to allow the transducer and/or receiver of embodiments of the system 1 to be positioned proximate to, and in some embodiments in physical contact with the syringe and to allow a patient to view the contents of the syringe 12 prior to operation.

While exemplary embodiments have been described herein, it is expressly noted that these embodiments should not be construed as limiting, but rather that additions and modifications to what is expressly described herein also are included within the scope of the present disclosure. Moreover, it is to be understood that the features of the various embodiments described herein are not mutually exclusive and can exist in various combinations and permutations, even if such combinations or permutations are not made express herein, without departing from the spirit and scope of the present disclosure. The contents of all references, patents, patent applications, and published patent applications cited throughout this application are incorporated herein by reference in their entirety.

The invention claimed is:

1. A syringe structural characterization system comprising:
   a transducer to output a first signal proximate to a syringe pre-filled with a fluid and incorporated in a housing substantially surrounding the syringe;
   a receiver to receive a response of the syringe to the first signal; and a processing device configured to control the transducer and the receiver to determine a structural characteristic of the syringe based on the response received by the receiver;

wherein at least one of the transducer and the receiver are configured to physically contact the syringe.

2. The syringe structural characterization system of claim 1, wherein the transducer is configured to vibrate at one or more frequencies and the receiver is configured to detect a syringe response to vibrations of the transducer.

3. The syringe structural characterization system of any one of claim 1, further comprising:

an adjustable stage operatively coupled to the transducer to position the transducer in proximity to the syringe.

4. The syringe structural characterization system of any one of claim 1, further comprising:

an adjustable stage operatively coupled to the receiver to position the receiver in proximity to the syringe.

5. The syringe structural characterization system of any one of claim 1, wherein the receiver is an acoustic sensor configured to measure the response.

6. The syringe structural characterization system of any one of claim 1, wherein the transducer and the receiver are positioned at a substantially similar location along a longitudinal axis of the syringe and radially offset from each other.

7. The syringe structural characterization system of claim 6, wherein the transducer and the syringe are radially offset by about one hundred eighty degrees.

8. The syringe structural characterization system of any one of claim 1, wherein the syringe is incorporated in an automatic injection device, the automatic injection device including the housing and the housing including openings through which the transducer and the receiver pass to position the transducer and the receiver in proximity to the syringe.

9. The syringe structural characterization system of any one of claim 1, wherein the structural characteristic is at least one of a crack and a scratch and the structural characteristic is detected based on a comparison between response parameters of the syringe and parameter limits corresponding to a characterization of one or more control syringes having like syringe attributes as the syringe.

10. The syringe structural characterization system of claim 9, wherein the response parameters include at least one of a peak amplitude of the response, a frequency at which the peak amplitude occurs, and a bandwidth of the response.

11. A system for characterizing a syringe based on structural characteristics of the syringe comprising:

a transducer configured to vibrate at one or more frequencies;

a receiver to detect a syringe response to vibrations of the transducer, the syringe pre-filled with a fluid and incorporated in a housing substantially surrounding the syringe; and a syringe characterization unit configured to characterize the response detected by the receiver;

wherein at least one of the transducer and the receiver are configured to physically contact the syringe.

12. The system of claim 11, wherein the syringe characterization unit identifies response parameters for the response and characterizes the response by generating a signature based on the response parameters.

13. The system of claim 12, wherein the response parameters include at least one of a peak amplitude of the response, a frequency at which the peak amplitude occurs, and a bandwidth of the response.

14. The system of claim 12, wherein the signature comprises at least one of an upper limit associated with a peak amplitude, a lower limit associated with a peak amplitude, an upper limit associated with a frequency at which a peak amplitude occurs, a lower limit associated with a frequency at which a peak amplitude occurs, an upper limit associated with a bandwidth of the response, and a lower limit associated with a bandwidth of the response.

15. A non-transitory computer readable medium storing processor executable instructions, wherein execution of the instructions by a processing device causes the processing device to:

control a transducer to vibrate at one or more frequencies;

receive a response of a syringe pre-filled with a fluid to vibrations of the transducer, the syringe incorporated in a housing surrounding the syringe, and at least one of the transducer and the receiver are configured to physically contact the syringe; and process the response to determine a structural characteristic of the syringe based on the response received the receiver.

16. The non-transitory medium of claim 15, wherein execution of the instructions by the processing device causes the processing device to compute a signature corresponding to the response of the syringe, the signature characterizing the syringe.

17. The non-transitory medium of claim 15, wherein the syringe is incorporated in an automatic injection device, the automatic injection device including the housing, and the housing including openings through which the transducer and the receiver pass to position the transducer and the receiver in proximity to the syringe.

18. The non-transitory medium of claim 15, wherein the structural characteristic is at least one of a crack and a scratch and execution of the instructions by the processing device causes the processing device to detected the structural characteristic based on a comparison between response parameters of the syringe and parameter limits corresponding to a characterization of one or more control syringes having like syringe attributes as the syringe.

19. A method of detecting a structural characteristic of a syringe comprising:

inducing vibrations in one or more syringes;

measuring a response of a syringe pre-filled with a syringe to the vibrations, the syringe is incorporated in a housing substantially surrounding the syringe;

positioning the transducer proximate to the syringe to induce vibrations in the syringe; and positioning the receiver proximate to the syringe to receive the response of the syringe to the vibrations;

wherein at least one the transducer and the receiver are configured to physically contact the syringe.

20. The method of claim 19, further comprising processing the response to identify response parameters including at least one of a peak amplitude of the response, a frequency at which the peak amplitude occurs, and a bandwidth of the response.

21. The method of claim 20, further comprising characterizing the syringe based on the response parameters.

22. The method of claim 21, wherein characterizing the syringe comprising generating at least one upper limit and at least one lower limit for at least one of the peak amplitude, the frequency at which the peak amplitude occurs, and the bandwidth of the response.

23. The method of claim 21, wherein the at least one upper limit and at least one lower limit are based on a statistical analysis of the response parameters for a plurality of syringes.

24. The method of claim 20, further comprising detecting a structural characteristic of the syringe based on the response parameters.

25. The method of claim 24, wherein the detecting the structural characteristic comprises comparing at least one of the response parameters to a predetermined limit.

* * * * *

UNITED STATES PATENT AND TRADEMARK OFFICE
CERTIFICATE OF CORRECTION

Page 1 of 1

PATENT NO. : 9,753,015 B2
APPLICATION NO. : 14/434050
DATED : September 5, 2017
INVENTOR(S) : Bardina et al.

It is certified that error appears in the above-identified patent and that said Letters Patent is hereby corrected as shown below:

In the Claims

Column No. 15, Line(s) No. 11-12, Claim 03, "of any one of claim 1," to read as --of claim 1,--

Column No. 15, Line(s) No. 16-17, Claim 04, "of any one of claim 1," to read as --of claim 1,--

Column No. 15, Line(s) No. 20-21, Claim 05, "of any one of claim 1," to read as --of claim 1,--

Column No. 15, Line(s) No. 23-24, Claim 06, "of any one of claim 1," to read as --of claim 1,--

Column No. 15, Line(s) No. 31-32, Claim 08, "of any one of claim 1," to read as --of claim 1,--

Column No. 15, Line(s) No. 39-40, Claim 09, "of any one of claim 1," to read as --of claim 1,--

Column No. 16, Line(s) No. 42, Claim 18, "to detected" to read as --to detect--

Column No. 16, Line(s) No. 50, Claim 19, "a syringe," to read as --a fluid--

Column No. 16, Line(s) No. 53, Claim 19, "positioning the transducer" to read as --positioning a transducer--

Column No. 16, Line(s) No. 55, Claim 19, "positioning the receiver" to read as --positioning a receiver--

Column No. 16, Line(s) No. 57, Claim 19, "wherein at least one the" to read as --wherein at least one of the--

Column No. 16, Line(s) No. 67, Claim 22, "syringe comprising" to read as --syringe comprises--

Signed and Sealed this
Eleventh Day of September, 2018

Andrei Iancu
*Director of the United States Patent and Trademark Office*